(12) United States Patent
Forkey et al.

(10) Patent No.: US 6,955,644 B2
(45) Date of Patent: Oct. 18, 2005

(54) AUTOCLAVABLE ENDOSCOPE

(75) Inventors: Richard E. Forkey, Westminster, MA (US); Robert N. Ross, Gardner, MA (US); Sheri A. Cruz, Gardner, MA (US)

(73) Assignee: Precision Optics Corporation, Gardner, MA (US)

( * ) Notice: Subject to any disclaimer, the term of this patent is extended or adjusted under 35 U.S.C. 154(b) by 129 days.

(21) Appl. No.: 10/383,236

(22) Filed: Mar. 6, 2003

(65) Prior Publication Data

US 2004/0176662 A1 Sep. 9, 2004

(51) Int. Cl.⁷ .................................................. A61B 1/04
(52) U.S. Cl. ........................ 600/133; 600/101; 600/138; 600/161
(58) Field of Search .................... 600/161, 101, 600/133, 138

(56) References Cited

U.S. PATENT DOCUMENTS

| | | | |
|---|---|---|---|
| 5,419,313 A | 5/1995 | Lemke | 128/6 |
| 5,569,163 A * | 10/1996 | Francis et al. | 600/133 |
| 5,599,278 A | 2/1997 | Hibbard | 600/133 |
| 5,601,525 A * | 2/1997 | Okada | 600/160 |
| 5,871,441 A | 2/1999 | Ishiguro et al. | 600/133 |
| 5,944,656 A | 8/1999 | Pollack et al. | 600/176 |
| 5,992,728 A | 11/1999 | Pollack et al. | 228/122.1 |
| 6,004,264 A | 12/1999 | Sano et al. | 600/178 |
| 6,080,101 A | 6/2000 | Tatsuno et al. | 600/112 |
| 6,099,467 A | 8/2000 | Kehr et al. | 600/167 |
| 6,146,326 A | 11/2000 | Pollack et al. | 600/141 |
| 6,390,972 B1 | 5/2002 | Speier et al. | 600/112 |
| 6,419,628 B1 | 7/2002 | Rudischhauser et al. | 600/161 |
| 6,425,857 B1 | 7/2002 | Rudischhauser et al. | 600/112 |
| 6,475,140 B1 | 11/2002 | Konstorum et al. | 600/141 |
| 6,478,731 B2 | 11/2002 | Speier et al. | 600/125 |
| 2002/0072653 A1 | 6/2002 | Ishizuka | 600/133 |
| 2002/0128539 A1 | 9/2002 | Higuma et al. | 600/133 |

* cited by examiner

Primary Examiner—Beverly M. Flanagan
Assistant Examiner—Matthew Kasztejna
(74) Attorney, Agent, or Firm—George A. Herbster

(57) ABSTRACT

A rigid endoscope includes an outer housing subassembly that supports an optics subassembly. The outer body subassembly includes concentric tubes with optical fiber for providing object illumination. The optics subassembly includes a tubular sheath sealed at both ends. A compression spring is positioned between a proximal most relay lens element and a distal most eyepiece element. The spring exerts a distally acting force on the elements of an optical objective and relay lens system. It also produces a proximally directed force on optical elements in the eyepiece. This minimizes differential thermal expansion stresses during autoclaving operations.

20 Claims, 8 Drawing Sheets

AUTOCLAVABLE ENDOSCOPE

BACKGROUND OF THE INVENTION

1. Field of the Invention

This invention relates to endoscopes and more particularly to endoscopes adopted for sterilization by autoclaving.

2. Description of Related Art

Endoscopes come in two basic forms. In one form the endoscope is flexible. Optical fibers transfer an image from an optical objective to an eyepiece or other viewing device. The fibers pixelate the image from the optical objective. Endoscopes of the second form are called rigid endoscopes. This invention, is applicable to rigid endoscopes. A rigid endoscope includes a tubular structure that carries an optical objective at a distal end and a relay lens system that transfers the image to a viewing device or eyepiece at a proximal end. Such devices provide better spatial resolution than flexible endoscopes do.

Rigid endoscopes are used in various surgical and diagnostic-medical procedures, so it is important that devices be capable of being sterilized. There are different ways to sterilize medical instruments. However, autoclaving is a preferred process. During this process, an endoscope is placed in a autoclave and steam is introduced to gradually raise the temperature to about 270° F. This temperature is maintained for some interval and then reduced in a controlled manner.

During this process, temperature differentials exist throughout the endoscope. Endoscopes, particularly rigid endoscopes, typically comprise materials characterized by different thermal coefficients of expansion. Consequently, during the autoclaving process it is possible for an endoscope to be subjected to different mechanical stresses. Experience has shown that repeated autoclaving of rigid endoscopes can damage seals whereupon steam can enter the endoscope with resultant condensation in the optical path distorting the image.

One approach for minimizing thermally induced stresses in rigid endoscopes has been to select materials that withstand all the temperatures involved with autoclaving and that minimize the effects of thermal expansion. For example, in U.S. Pat. No. 5,599,278 to Hibbard a housing, eyepiece, insertion tube, windows and light pipe are comprised of materials which withstand a temperature of at least 1200° F., well above a typical autoclaving temperature. In addition, components are composed of materials having a low thermal expansion coefficient with high thermal conductivity and high thermal shock resistance.

U.S. Pat. No. 5,944,656 to Pollack et al. discloses an endoscope in which cylindrical spacers position various lenses along an optical path in a tubular housing. Proximal and distal windows seal the ends of the housing. The windows are brazed to the endoscope thereby eliminating any adhesives, epoxies or other organic materials. In one embodiment, the relay lens system includes spacers with slots so they can flex individually like a bellows. Consequently the spacers maintain compression on the lenses over a varying temperature range to ensure that they will not tilt when the endoscope is thermally stressed.

In addition endoscopes are often subject to mechanical shock as a result of mishandling. For example, it is not unusual for an endoscope to be dropped. The Pollock et al. patent introduces spacers with lateral slots. These spacers are stated to act as gimbal springs to allow the spacers to flex slightly like a bellows. The spacers maintain compression on the lenses over varying temperature range without canting or tilting during expansion or contraction. However, such spacers, while effective for absorbing long term stresses as introduced by autoclaving, do not readily absorb transient shocks, such as the shocks introduced when an endoscope strikes the floor or other object. The effect of such transient shocks would be the same regardless of whether the sleeves contain lateral slots.

SUMMARY

Therefore it is an object of this invention to provide an endoscope that is adapted for repeated autoclaving operations.

Another object of this invention is to provide an endoscope that has a reduced susceptibility to damage by shock.

Still another object of this invention is to provide an endoscope that is adapted for repeated autoclaving operations and has a reduced susceptibility to damage by mechanical shock.

Still another object of this invention is to provide an endoscope that facilitates repair should damage occur.

Yet still another object of this invention is to provide an endoscope that is easy to manufacture, facilitates necessary adjustments during manufacture and is readily disassembled and reassembled for repair.

In accordance with one aspect of this invention an endoscope includes an optics subassembly. The optics subassembly comprises a tubular sheath that carries first, second and third sets of optical elements. The first optical element set forms an optical objective at the distal end of the sheath. The second optical element set forms an eyepiece at the proximal end of the sheath. The third optical element set forms a relay lens system in the tubular sheath intermediate the objective and the eyepiece. An expansible structure in the tubular sheath positioned between the second and third optical element sets biases the first and third optical element set toward the distal end of the tubular sheath and the second optical element set toward the proximal end of the tubular sheath.

In accordance with another aspect of this invention an endoscope extends between distal and proximal ends and comprises an outer housing subassembly, an optics subassembly and structure for capturing the optics subassembly in the outer housing subassembly. The optics subassembly includes a tubular sheath that extends through a central lumen in the outer housing subassembly. The tubular sheath has sealed windows at each of the proximal and distal ends. An optical objective is slidably mounted in the distal end of the tubular sheath. An eyepiece is slidably mounted in the tubular sheath at the proximal end. A relay lens system is slidably mounted in the tubular sheath intermediate the optical objective and the eyepiece for conveying an image from the optical objective to the eyepiece. An expansible structure in the tubular sheath is positioned between the relay lens system and the eyepiece for biasing the optical objective and relay lens system toward the distal end and the eyepiece toward the proximal end.

In accordance with another aspect of this invention, an endoscope has distal and proximal ends and lies along an optical axis. Inner and outer radially spaced concentric tubes extend along the optical axis. Light transferring optical fiber distributed between the tubes projects light from a source to illuminate an object. A tubular sheath extends along the optical axis inside the inner radially spaced concentric tube. Distal and proximal windows seal the distal and proximal ends of the tubular sheath. An optical objective is slidably mounted within the tubular sheath near the distal window to produce an image of an object illuminated by light from the fiber. A relay lens system includes a plurality of optical elements slidably mounted within the tubular sheath for transferring the image produced by the objective to the proximal end. One end of an axially expandable cylindrical structure abuts the proximal most optical element in the relay lens system and an aperture spacer slidably mounted within the tubular sheath proximally of the axially expandable structure. An eyepiece doublet lens slidably mounted within the tubular sheath is positioned proximally of the aperture spacer. An axially adjustable end stop provides adjustment of the position of the doublet lens and the aperture spacer during manufacture.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
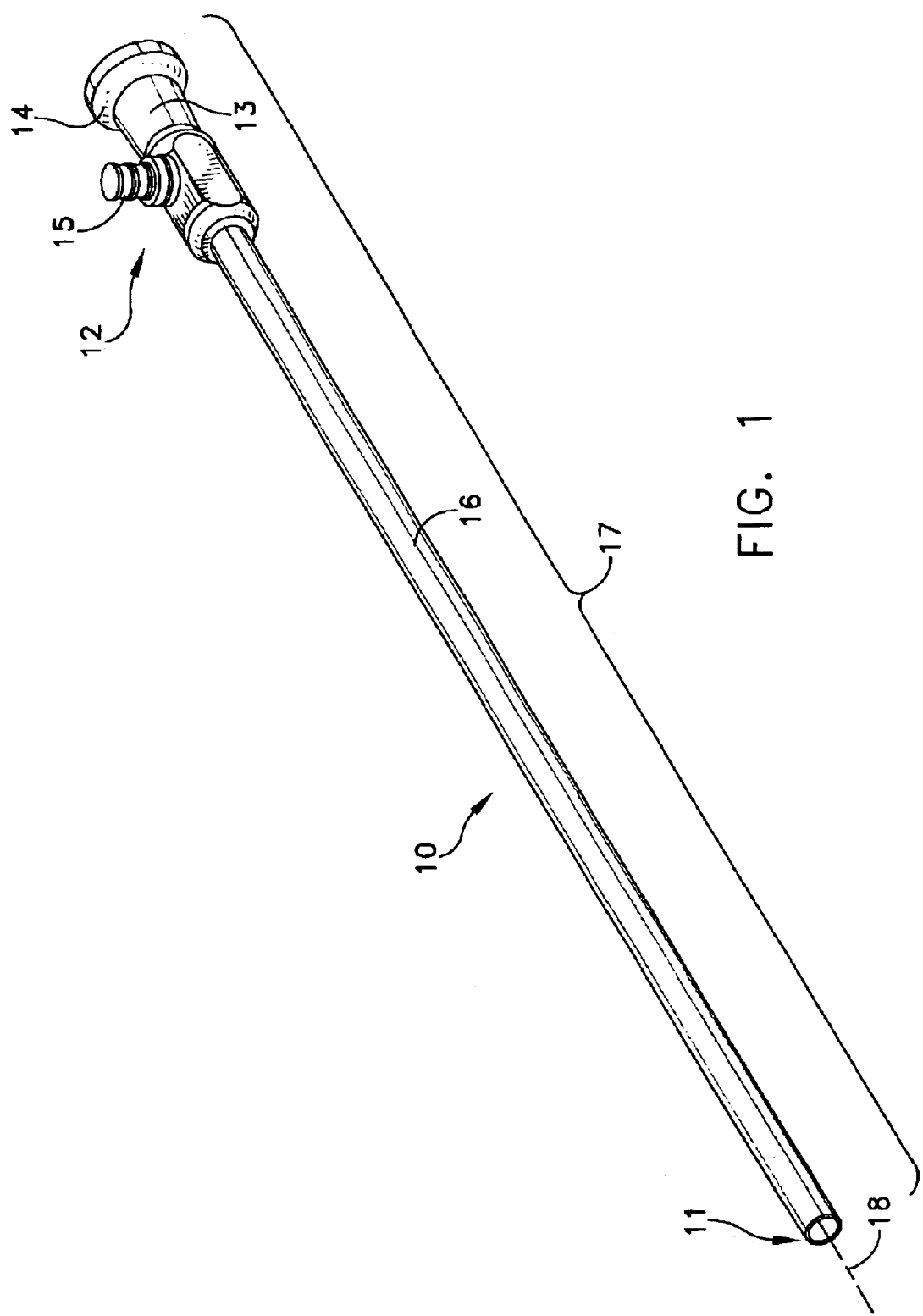
FIG. 1 is a perspective view of an endoscope constructed in accordance with this invention.

FIG. 1 depicts an endoscope 10 as it appears to medical personnel for use. It extends between a distal end 11, the end closest to the object to be imaged and a proximal end 12, the end closest to the person using the device. In this view an individual sees an optical body 13 with an eyecup 14 through which the image is viewed. A fiber post 15 receives an output connection from an illumination source thereby to provide light for transmission through optical fiber to illuminate the object being imaged. An outer tube 16 extends from the optical body. All of these elements constitute components of an outer housing subassembly 17 that extends along an optical axis 18.

Figure 2:
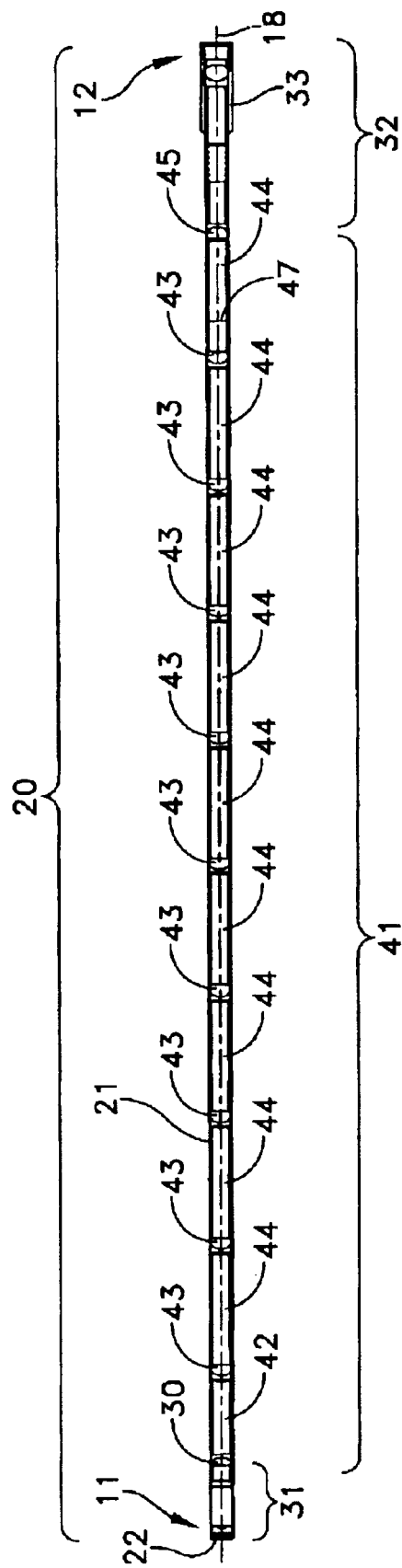
FIG. 2 is a sectional view of an optics subassembly that is contained within the endoscope of FIG. 1 and FIGS. 2A and 2B are enlarged sectional views at the distal and proximal ends of the optics subassembly of FIG. 2.
Figure 2A:
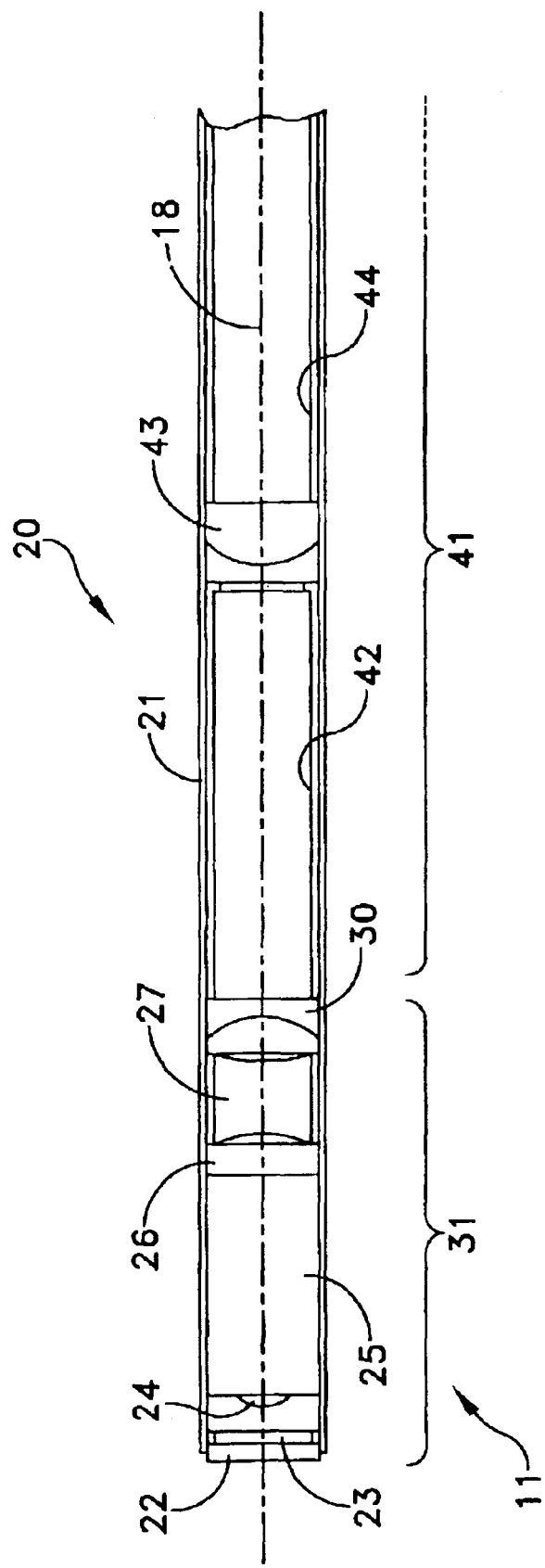
Figure 2B:
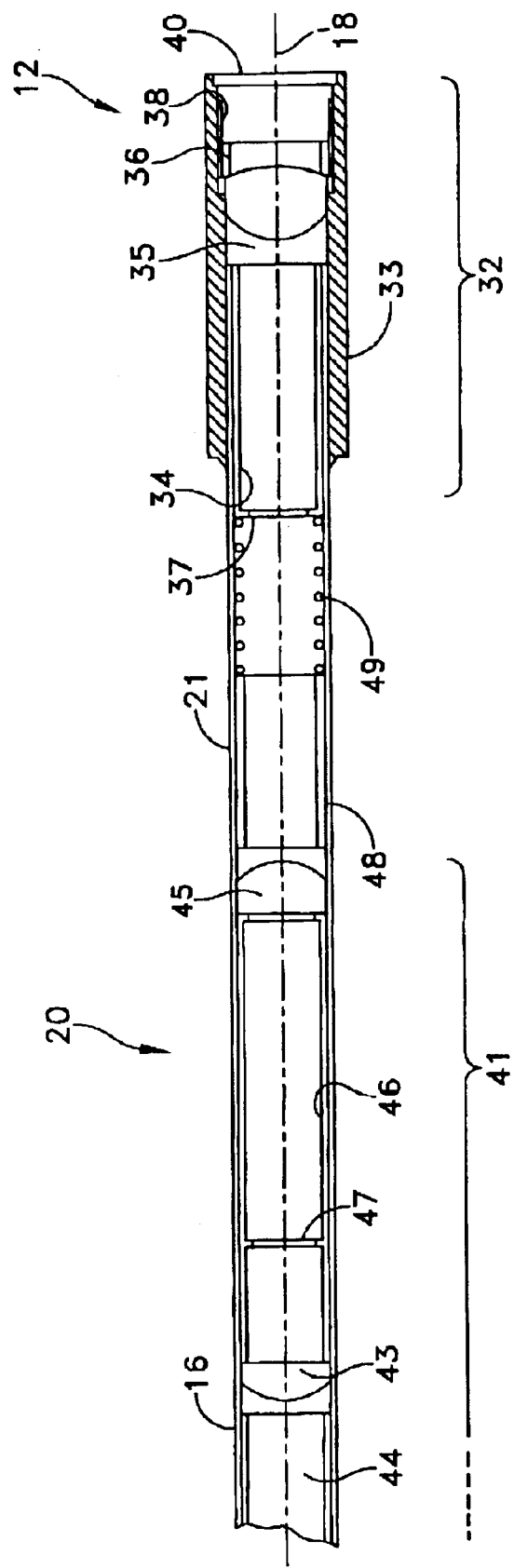

The endoscope 10 also houses an optics subassembly 20 as shown in FIG. 2. The optics subassembly 20 also extends between the distal end 11 and proximal end 12. FIGS. 2A and 2B depict portions of the optics subassembly 20 at the distal and proximal ends 11 and 12 in enlarged cross-sections, respectively. Specifically the optics subassembly 20 includes a tubular sheath 21 that extends along the optical axis 18. As clearly seen from FIG. 2A, a distal window 22 seals the tubular sheath 21 at the distal end 11. The distal optical window 22 can be formed of any material that will withstand autoclaving temperatures. Sapphire windows are particularly suited. Brazing or soldering or other processes seal the distal window 22 to the tubular sheath 21. The brazing or soldering materials are selected to minimize any differences in radial thermal expansion. An annular spacer 23 can also be bonded to the interior of the tubular sheath 21 for further strength and to space a planoconcave lens 24 at an appropriate position along the optical axis 18.

The planoconcave lens 24, a rod lens 25, a planoconvex lens 26, a lens spacer 27 and an objective doublet lens 30 constitute one embodiment of a first optical element set that forms an optical objective 31 in the tubular sheath 21 at the distal end 11. As known, an optical objective 31 forms an image of an object lying on an extension of the optical axis 18. The optical objective 31 may have any of a variety of other embodiments. For example, the specific optical objective 31 in FIG. 2A images an object that lies on an extension of the optical axis 18. Other optical objectives might image an object at some angle off the optical axis 18, such as 30° or 45°.

A second optical element set forms an eyepiece 32 in the proximal end 12 of the optics subassembly 20. As shown in FIGS. 2 and 2B, the eyepiece 32 extends into the tubular sheath 21 from the proximal end 12 and an axially extending collar 33 that is soldered or brazed to the tubular sheath 21. Optical elements that form the eyepiece include an aperture/spacer 34, an eye lens 35 and a retainer 36. The aperture/spacer 34 has a reduced diameter field stop 37. The overall length of the aperture/spacer 34 is selected to space the field stop 37 an appropriate distance from the eye lens 35. The retainer 36 is externally threaded to engage internal threads 38 at the proximal end of the collar 33. This retainer 36 provides a positive end stop for the eyepiece elements and, as described later, provides adjustment during manufacture or repair. A proximal window 40 seals the proximal end of the collar 33 like the distal window 22 seals the distal end of the tubular sheath 21.

A third optical element set forms a relay lens system 41 intermediate the first and second optical element sets that constitute the optical objective 31 and the eyepiece 32. As known, a relay lens system transfers an image from an optical objective to an eyepiece. Referring first to FIGS. 2 and 2A, a first spacer 42 positions a first relay doublet lens 43 relative to the objective doublet lens 30. Cylindrical intermediate lens spacers 44 and additional relay doublet lenses 43 constitute additional optical elements that are spaced along the optical axis 18 in order to a proximal most relay doublet lens 45; that is, the relay doublet lens 45 closest to the proximal end 12. Generally the intermediate lens spacers 44 have the same configuration and length throughout the relay lens system. However, in FIGS. 2 and 2B an end lens spacer 46 includes a glare stop 47 and spaces the proximal most relay doublet lens 45 from an adjacent distally located relay lens doublet 43. The construction and operation of such relay lens systems are known in the art. Many modifications could be made to the specific lens and spacer configuration shown in FIG. 2.

Still referring to FIGS. 2A and 2B, a sleeve spacer 48 abuts the proximal side of the proximal most relay lens element 45 and a compression spring 49 lies between the sleeve spacer 40 and the aperture/spacer 34. As described later, the compression spring 49 acts to assure correct positioning of the optical elements in the tubular sheath 21 and to minimize stresses introduced by thermal expansion during autoclaving.

It will now be helpful to understand the manufacture of such an optics subassembly 20. After the distal optical window 22 and any optional spacer 23 are soldered or brazed to the interior of the tubular sheath 21, the remaining optical elements including lenses and lens spacers of the optical objective 31, the relay lens system 41 and the eyepiece 32 including the spacer 48 and spring 49 are inserted in order from the open proximal end through the collar 33. The retainer 36 is then threaded into the collar 35 to advance the eye lens 36 and the aperture/spacer 34. This compresses the spring 49. The retainer 36 can be adjusted and positioned along the threaded portion of the collar 33 until the image produced at the field stop 37 is in focus. Once the unit is focussed, the proximal optical window 40 is sealed onto the end of the collar 33 in the same manner as the distal optical window 22 was applied to the distal end of the tubular sheath 21.

As will now be apparent, all the optical elements that constitute the optical objective 31, the eyepiece 32, and the relay lens system 41 are slidably mounted in the tubular sheath 21 along the optical axis 18. As the retainer 36 advances distally, it compresses the spring 49. Consequently, the spacer 48 and spring 49 act as an expansible element that applies a distally directed force to seat all the optical elements in the optical objective and relay lens system against the spacer 23 or distal optical window 22. The spring 49 also applies a proximally directed force to the optical elements in the eyepiece 32 to seat these optical elements against the retainer 36. During autoclaving, the spring 49 allows the tubular sheath 21 to expand and contract axially without any effect on the optical elements in the tubular sheath 21. Likewise individual optical elements, like the various spacers can expand and contract axially without any effect on the tubular sheath 21. Thus such expansion and contraction produces only minimal stresses.

The only seals in the optics subassembly are formed at the circumference of the distal window 22 and proximal window 40. Axially directed forces introduced during autoclaving have a minimal effect on seal integrity and life because the axial length of the seal is very short. The effect of radially directed forces can be minimized by the selection of materials and the configuration of the sealing materials. As a result, an optics subassembly 20 can be subjected to repeated autoclaving without damage to the seals at the distal window 22 and the proximal window 40.

As previously indicated, the position of the aperture spacer 34 and eye lens 35 are adjusted during manufacture for focusing the image from the relay lens system 41. Positioning the spring 49 intermediate the proximal most relay lens doublet 45 and the aperture spacer 47 allows this adjustment to be made without influencing the position of any optical elements in the optical objective 31 or relay lens system 41.

If an endoscope with an optics subassembly 20 is mishandled, mechanical shock has a minimal effect on the integrity of the optics subassembly 20. Although such shock forces may cause a transient axial displacement of various optical elements within the tubular sheath 21, the spring 49 repositions those elements in their original positions and maintains the focus of the optics assembly immediately upon the return of normal conditions.

The construction of the optics subassembly 20 also facilitates any needed repair. It is a straightforward process merely to heat and remove the proximal optical window 40, unscrew the retainer 36 and allow all the elements with the exception of the distal optical window 22 and the adjacent optional spacer 23 to slide from the tubular sheath for inspection and repair. After any necessary repair the optical elements can merely be reloaded in their original sequence. Then the retainer 36 is threaded to refocus the optics subassembly 20. The proximal optical window 40 is soldered or brazed to reseal the optics subassembly 20.

Figure 3A:
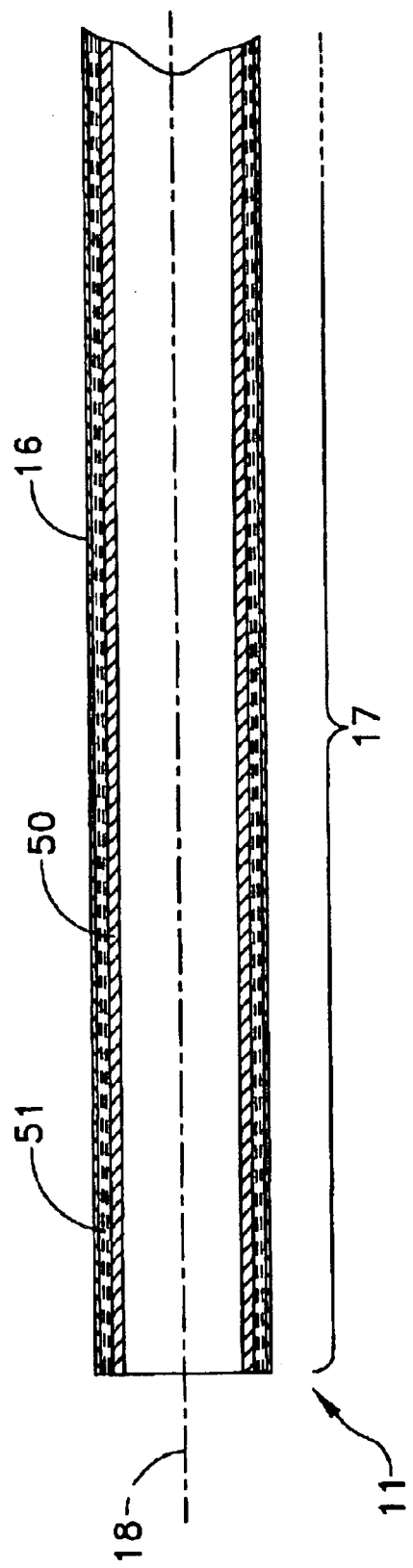
FIGS. 3A and 3B are enlarged sectional views at the distal and proximal ends of an outer subassembly depicted in FIG. 1.
Figure 3B:
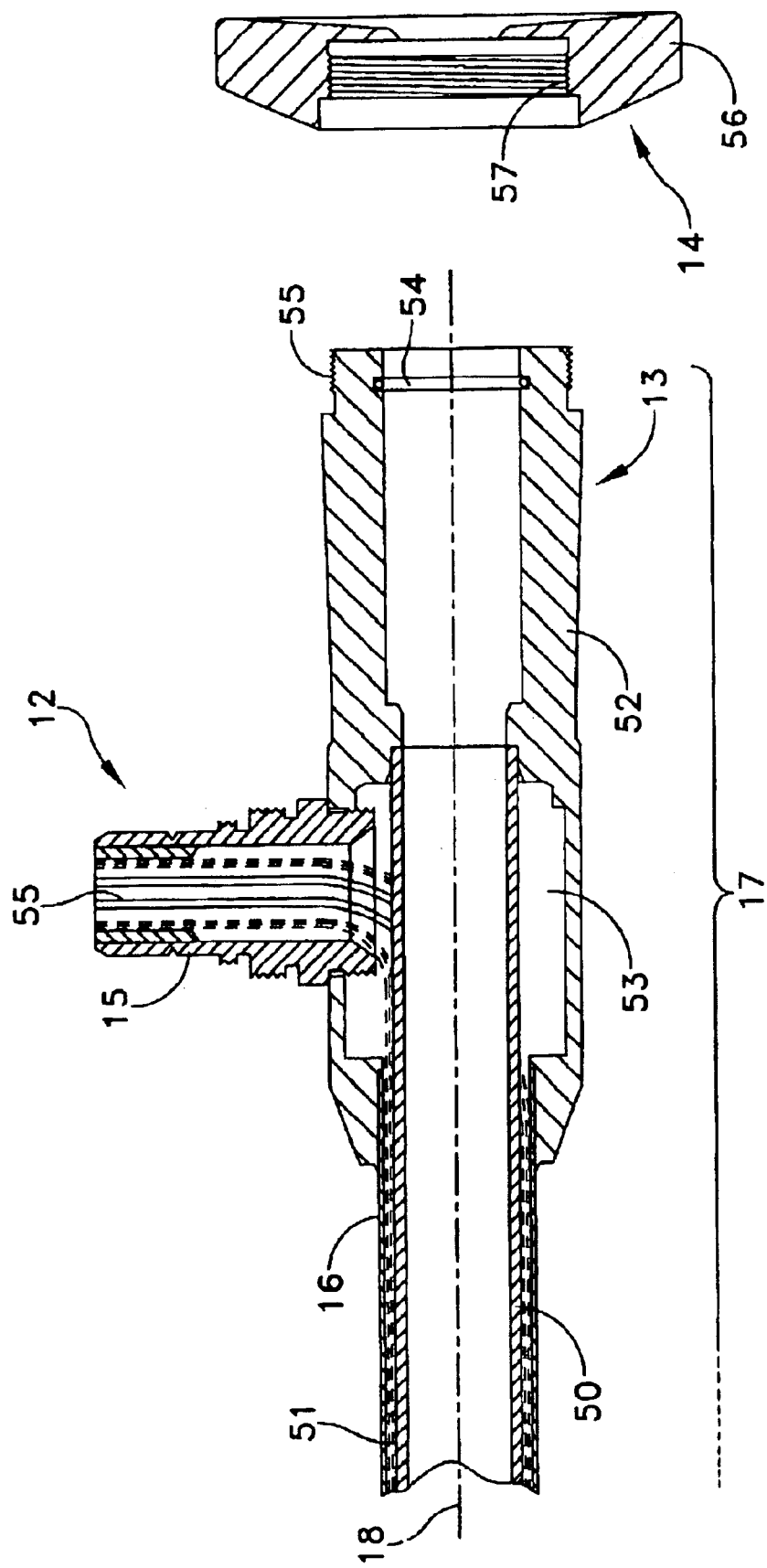

This division of the endoscope into the optics subassembly 20 and the outer housing subassembly 17 facilitates manufacturing. Referring to FIGS. 3A and 3B, the outer tube 16 of the outer housing subassembly 17 is formed about a concentric, radially spaced inner tube 50 to form an annular space between the outer and inner tubes 16 and 50. At the distal end shown in FIG. 3A optical fiber 51 fills the annular space.

At the proximal end the outer tube 16 and inner tube 50 attach to a proximal body 52 that is shown as a one-piece device in FIG. 3B, but could be formed of multiple parts to adapt different components to a specific embodiment. A channel 53 allows the individual optical fibers 51 to be gathered into a cylindrical bundle 54 that terminates in the fiber post 15. The optical fibers 51 receive light delivered from an external source at the fiber post 15 and illuminate an object at the distal end 11.

The proximal body 52 also terminates as its proximal end with an internal O-ring 55 and an externally threaded end portion 56 to receive the eyecup 14 that includes a body portion 57 with internal threads 58. The use of eyecups with their attachment to proximal bodies is well know in the art.

Figure 4A:
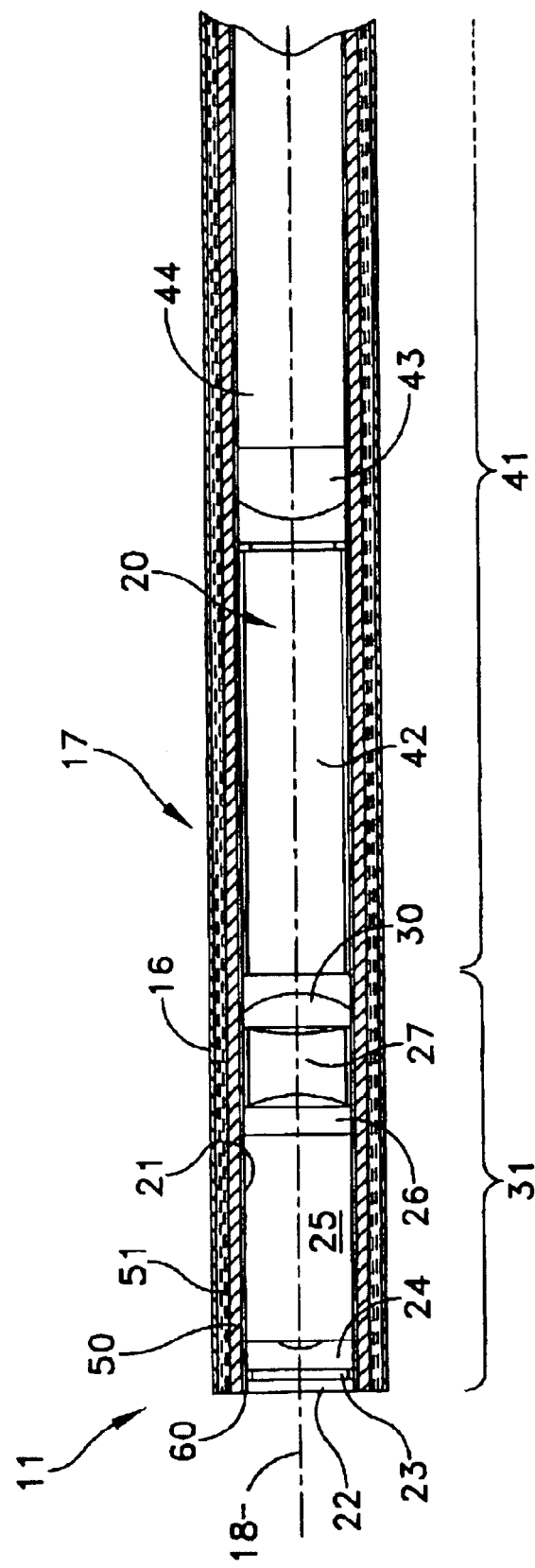
FIGS. 4A and 4B are enlarged cross-sectional views taken through the assembled endoscope of FIG. 1 at the distal and proximal ends, respectively.
Figure 4B:
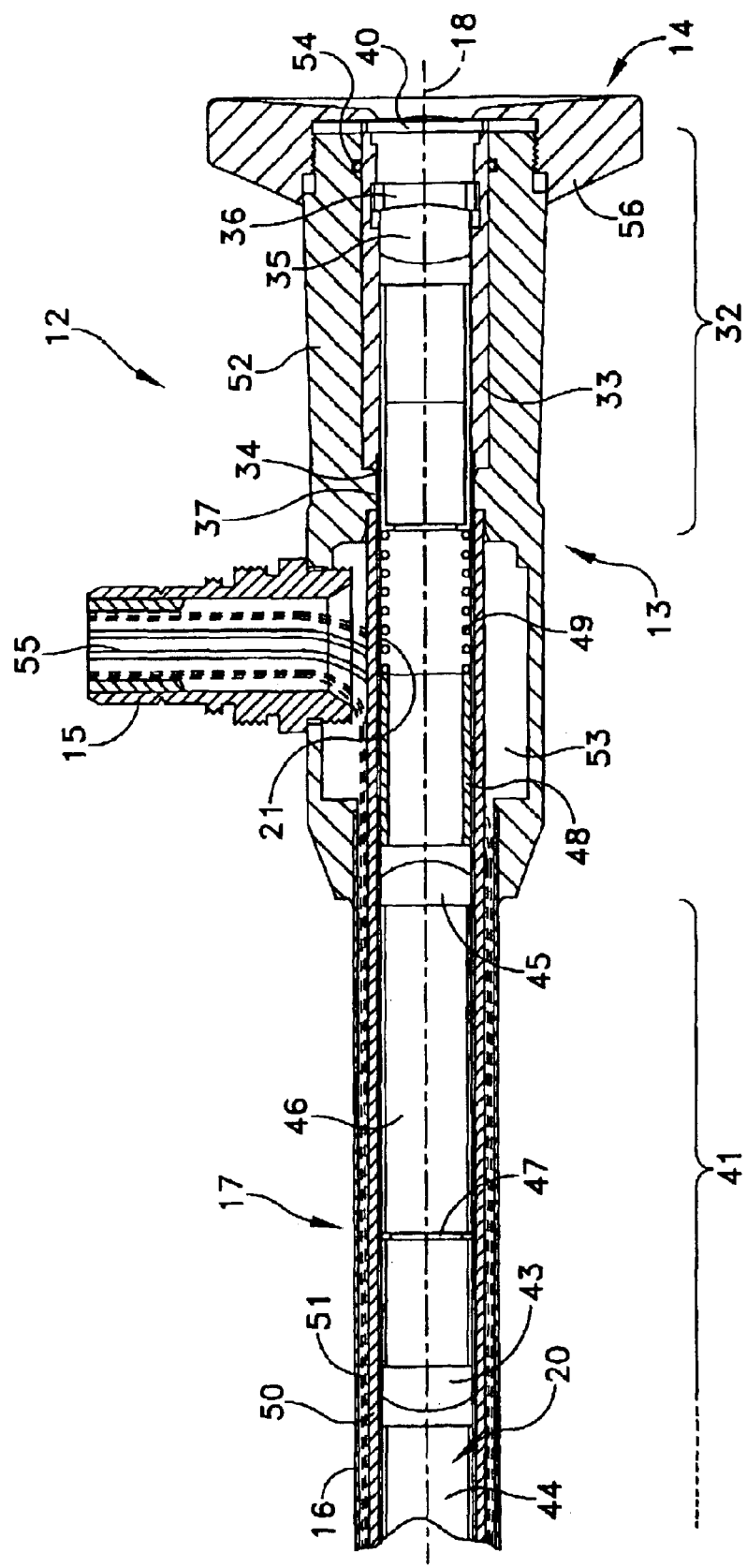

Optics subassembly 20 and outer housing subassembly 17 constructed in accordance with this invention also enable a manufacturer to inventory these subassemblies for a variety of applications. For example, different optics subassemblies 20 can have different viewing angles or other optical characteristics. When a customer wishes to purchase an endoscope, the manufacturer selects an optics subassembly 20 with the proper optical characteristics and an outer housing subassembly 17. Then the optics subassembly 20 is inserted along the optical axis 18 through the inner tube 50 until it is seated, particularly as shown in FIGS. 4A and 4B. As all the critical optical elements are within the sealed tubular sheath 21, the distal end can be fixed by the application of an epoxy or solder seal 60 between the outer surface of the optical tube main body 21 and the inner surface of the inner tube 50. At the proximal end the O-ring 54 engages the collar 33 to provide a peripheral seal. When this is complete the eyecup 14 is threaded onto the proximal body 52 to complete the assembly of the endoscope 10. Any leakage through the epoxy or solder seal 60 end or past the O-ring 55 does not migrate into the optical path, so such leakage can be tolerated. Further, as previously indicated if a distal window 22 or proximal window 40 were to fail, the seals are replaced easily.

As will now be apparent an endoscope 10 constructed in accordance with this invention meets all the objectives of this invention. The optics assembly 20 is constructed with only two solid seals. This, coupled with the use of the expansible member between the various sets of optical elements and the lack of any bonding between the individual optical elements and a tubular sheath minimize any damage due to differential thermal expansion encountered during repeated autoclaving. The most significant forces, generated as a result of differential thermal expansion, are radial forces at the distal and proximal ends between the windows and tubular sheath that are easily compensated. The use of a single compression spring assures the proper relationships exist between the elements that need to be focused and the remaining optical elements within the optics subassembly. Further, the use of such a spring minimizes any damage that might be caused by shock as a result of mishandling the endoscope.

Variations of the various components of the disclosed endoscope have been discussed. Essentially FIGS. 1 through 4B depict one specific embodiment of an endoscope embodying the invention. Different lens configurations for the optical objective, for the eyepiece and for the relay lens system can all be substituted while still attaining some or all of the benefits of this invention. It will be apparent that many other modifications could also be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. An optics subassembly for an endoscope having a distal end and a proximal end comprising:
   A) a tubular sheath,
   B) a first optical element set forming an optical objective in said tubular sheath at the distal end thereof,
   C) a second optical element set forming an eyepiece in said tubular sheath at the proximal end thereof,
   D) a third optical element set forming a relay lens system in said tubular sheath intermediate said first and second optical element sets, each of said optical elements in being axially displaceable with respect to said sheath, and
   E) expansible means in said tubular sheath between said second and third optical element for biasing said first and third optical element toward the distal end and said second optical element set toward the proximal end of said sheath.

2. An optics subassembly as recited in claim 1 wherein said sheath includes optical windows sealed to said sheath at the distal and proximal ends thereof.

3. An optics subassembly as recited in claim 2 wherein said expansible means comprises a compression spring.

4. An optics subassembly as recited in claim 2 wherein said expansible means comprises a compression spring and a sleeve spacer.

5. An optics subassembly as recited in claim 2 wherein said second optical element set comprises a plurality of eyepiece optical elements and said third optical element set include relay lens elements and intermediate spacer elements and wherein said expansible means comprises:
   A) a sleeve spacer that bears against a relay lens element, and
   B) a compression spring with opposite ends in contact with said sleeve spacer and a distal most eyepiece element in said second optical element set, respectively.

6. An optics subassembly as recited in claim 5 wherein said relay lens system comprise a plurality of doublet lenses and said sleeve spacer abuts said proximal most doublet lens.

7. An optics subassembly as recited in claim 1 wherein elements in said second optical elements are taken from the group consisting of lenses, lens spacers, field stops and apertures and wherein said expansible means contacts one of said optical elements.

8. An optics subassembly as recited in claim 7 wherein said expansible means comprises a compression spring.

9. An optics subassembly as recited in claim 7 wherein said expansible means comprise a compression spring and a sleeve spacer.

10. A optics subassembly as recited in claim 7 wherein said expansible means comprises a sleeve spacer that bears against a proximal most element in the relay lens system and a compression spring intermediate said sleeve spacer and an element in said second optical element set.

11. An endoscope having distal and proximal ends and comprising;
    A) an outer housing subassembly having a central lumen therethrough, and
    B) an optics subassembly in said lumen including:
       i) a tubular sheath extending through the central lumen and having sealed windows at each of the distal and proximal ends,
       ii) an optical objective slidably mounted in the distal end of said tubular sheath for forming an image of an object,
       iii) an eyepiece slidably mounted in said tubular sheath at the proximal end thereof for presenting an image for viewing,
       iv) a relay lens system slidably mounted in said tubular sheath intermediate said optical objective and eyepiece for conveying an image from said optical objective to said eyepiece, and
       v) expansible means including a compression spring, said expansible means being slidably mounted in said tubular sheath between and in contact with said relay lens system and said eyepiece for biasing said optical objective and said relay lens system toward the distal end and said eyepiece toward the proximal end of said sheath thereby to compensate for any thermal expansion and contraction of said objective, eyepiece and relay lens system, and
    C) means for capturing said optics subassembly in said outer housing subassembly.

12. An endoscope as recited in claim 11 wherein said expansible means comprises a sleeve spacer slidably mounted in said tubular sheath in contact with one end of said compression spring.

13. An endoscope as recited in claim 12 wherein said compression spring is positioned proximally of said sleeve spacer.

14. An endoscope as recited in claim 11 wherein said eyepiece and relay lens system comprise a plurality of lens elements disposed along an optical axis and said expansible means includes:
    A) a sleeve spacer that bears against a proximal most optical element in said relay lens system,
    B) said compression spring being intermediate said sleeve spacer and a distal most optical element in said eyepiece.

15. An endoscope as recited in claim 14 wherein said sleeve spacer abuts a doublet lens of said relay lens system.

16. An endoscope as recited in claim 14 wherein said expansible mean contacts a field stop in said eyepiece.

17. An endoscope as recited in claim 16 including axially displaceable adjustment means in maid optics subassembly for adjusting the compression of said compression spring.

18. An endoscope as recited in claim 16 wherein said outer housing subassembly comprises inner and outer, radially spaced concentric tubes and optical fiber distributed in the annular space between said concentric tubes at the distal end of said endoscope.

19. An endoscope as recited in claim 16 wherein said eyepiece comprises a distally positioned aperture spacer an a proximally positioned doublet eye lens and said expansible means comprises a sleeve spacer that bears against a proximal most lens in said relay lens system and a compression spring intermediate said sleeve spacer and said aperture spacer.

20. An endoscope having distal and proximal ends lying along an optical axis and comprising:

A) inner and outer radially spaced concentric tubes extending along the optical axis and including light-transferring optical fiber distributed between said tubes, said optical fiber being adapted for receiving light from a source and projecting light from the distal end of said endoscope to illuminate an object, B) a tubular sheath extending along the optical axis, C) distal and proximal windows sealed across the distal and proximal ends of said tubular sheath thereby to seal the interior of said sheath, D) an optical objective slidably mounted within said tubular sheath near said distal window, said optical objective producing an image of an object illuminated by light from said fiber, E) a relay lens system including a plurality of optical elements slidably mounted within said tubular sheath for transferring the image produced by said optical objective to the proximal end of said tubular sheath, F) an axially expandable cylindrical structure having a distal end abutting the proximal most optical element in said relay lens system, G) an aperture spacer slidably mounted within said tubular sheath proximally of said axially expandable structure with a distal end in contact with a proximal end of said axially expandable cylindrical structure, H) an eyepiece doublet lens slidably mounted within said tubular sheath proximally of said aperture spacer in contact therewith, and I) an axially adjustable end stop for axially adjusting the position of said doublet lens and said aperture spacer relative to said relay lens system whereby said expandable cylindrical structure compensates for axial displacement of said eyepiece during manufacture of said endoscope.

* * * * *